US00PP36842P2

(12) United States Plant Patent
Chojnacki

(10) Patent No.: US PP36,842 P2
(45) Date of Patent: Jul. 22, 2025

(54) ***ACER* TREE NAMED 'Autken1'**

(50) Latin Name: *Acer palmatum*
Varietal Denomination: Autken1

(71) Applicant: Brian Chojnacki, Park Hill, OK (US)

(72) Inventor: Brian Chojnacki, Park Hill, OK (US)

( * ) Notice: Subject to any disclaimer, the term of this patent is extended or adjusted under 35 U.S.C. 154(b) by 0 days.

(21) Appl. No.: 18/738,040

(22) Filed: Jun. 9, 2024

(51) Int. Cl.
*A01H 5/00* (2018.01)
*A01H 6/00* (2018.01)

(52) U.S. Cl.
USPC ..... Plt./224
CPC ..... *A01H 6/00* (2018.05)

(58) Field of Classification Search
USPC ..... Plt./224
CPC ..... A01H 5/00
See application file for complete search history.

*Primary Examiner* — Kent L Bell
(74) *Attorney, Agent, or Firm* — C. Anne Whealy

(57) ABSTRACT

A new and distinct cultivar of Japanese Maple tree named 'Autken1', characterized by its upright to outwardly spreading plant form; moderately vigorous growth habit; freely branching habit with numerous lateral branches providing a full and densely foliated appearance; leaves with narrow and pointed lobes and finely-serrated margins; and dark reddish brown-colored leaves that become bright cherry red in color during the autumn.

2 Drawing Sheets

Figure 1:
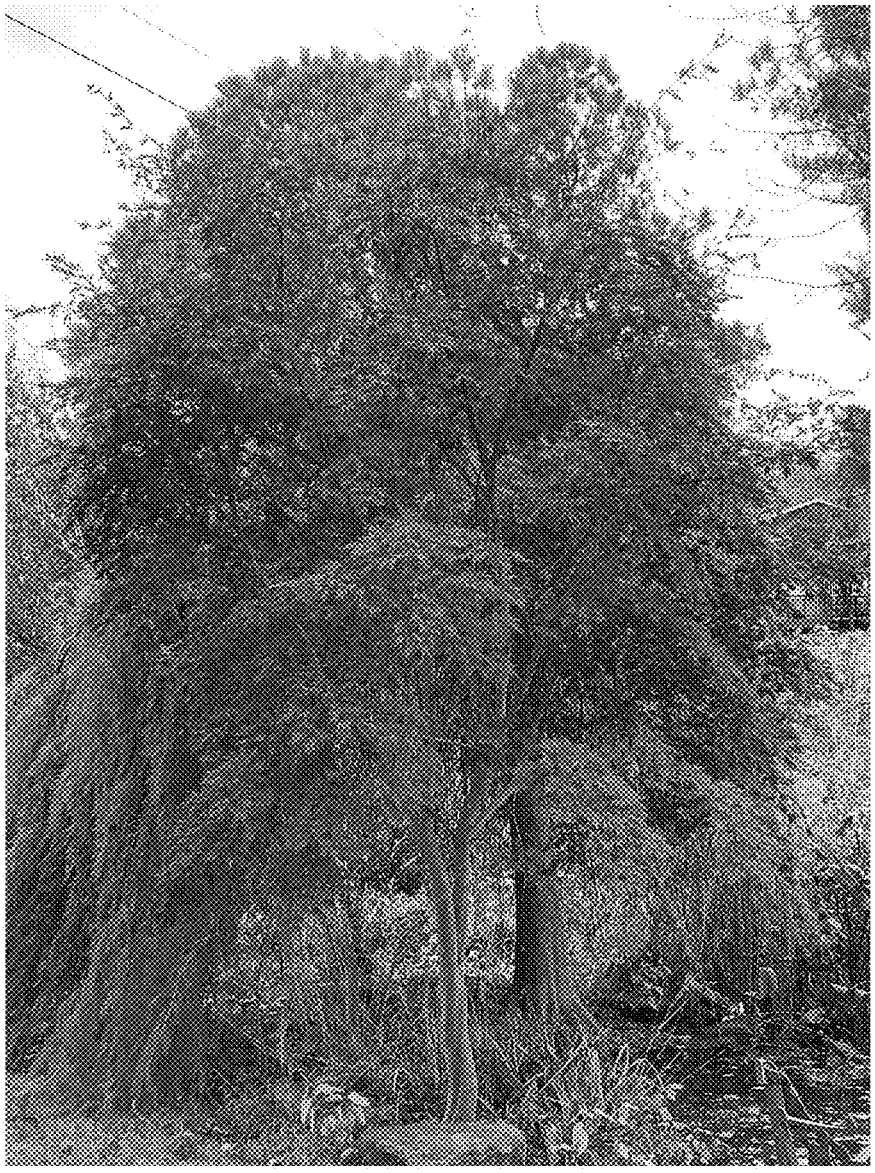

Botanical designation: *Acer palmatum.*
Cultivar denomination: 'AUTKEN1'.

BACKGROUND OF THE INVENTION

The present invention relates to a new and distinct cultivar of *Acer* tree, botanically known as *Acer palmatum*, commercially referred to as a Japanese Maple tree and hereinafter referred to by the name 'Autken1'.

The new Japanese Maple tree is a naturally-occurring whole plant mutation of an unnamed selection of *Acer palmatum*. The new Japanese Maple tree was discovered and selected by the Inventor as a single plant from within a population of plants of the unnamed selection in a controlled environment in Cherokee County, Oklahoma in 2007.

Asexual reproduction of the new Japanese Maple tree by grafting in a controlled environment in Cherokee County, Oklahoma since 2010 has shown that the unique features of this new Japanese Maple tree are stable and reproduced true to type in successive generations.

SUMMARY OF THE INVENTION

Trees of the new Japanese Maple have not been observed under all possible combinations of environmental and cultural conditions. The phenotype may vary somewhat with variations in environmental conditions such as temperature and light intensity without, however, any variance in genotype.

The following traits have been repeatedly observed and are determined to be the unique characteristics of 'Autken1'. These characteristics in combination distinguish 'Autken1' as a new and distinct Japanese Maple tree:

1. Upright to outwardly spreading plant form.
2. Moderately vigorous growth habit.
3. Freely branching habit with numerous lateral branches providing a full and densely foliated appearance.

4. Leaves with narrow and pointed lobes and finely-serrated margins.
5 Dark reddish brown-colored leaves that become bright cherry red in color during the autumn.

Trees of the new Japanese Maple can be compared to trees of the mutation parent selection. Trees of the new Japanese Maple differ primarily from trees of the mutation parent selection in the following characteristics:

1. Leaves of plants of the new Japanese Maple have narrower lobes than leaves of plants of the mutation parent selection.
2. Leaves of plants of the new Japanese Maple have more finely serrated margins than leaves of plants of the mutation parent selection.
3. Leaves of plants of the new Japanese Maple are darker reddish brown in color during the summer and brighter red in color during the autumn than leaves of plants of the mutation parent selection.

Trees of the new Japanese Maple can be compared to trees of *Acer palmatum* 'Bloodgood', not patented. Trees of the new Japanese Maple and 'Bloodgood' differ primarily in the following characteristics:

1. Leaves of plants of the new Japanese Maple have narrower lobes than leaves of plants of 'Bloodgood'.
2. Leaves of plants of the new Japanese Maple have more finely serrated margins than leaves of plants of 'Bloodgood'.
3. Leaves of plants of the new Japanese Maple are darker reddish brown in color during the summer and brighter red in color during the autumn than leaves of plants of 'Bloodgood'.

Trees of the new Japanese Maple can also be compared to trees of *Acer palmatum* 'Emperor 1', not patented. Trees of the new Japanese Maple and 'Emperor 1' differ primarily in the following characteristics:

1. Leaves of plants of the new Japanese Maple have narrower lobes than leaves of plants of 'Emperor 1'.

2. Leaves of plants of the new Japanese Maple have more finely serrated margins than leaves of plants of 'Emperor 1'.
3. Leaves of plants of the new Japanese Maple are darker reddish brown in color during the summer and brighter red in color during the autumn than leaves of plants of 'Emperor 1'.

BRIEF DESCRIPTION OF THE PHOTOGRAPHS

The accompanying colored photographs illustrate the overall appearance of the new Japanese Maple tree showing the colors as true as it is reasonably possible to obtain in colored reproductions of this type. Colors in the photographs may differ slightly from the color values cited in the detailed botanical description which accurately describe the colors of the new Japanese Maple tree.

The photograph on the first sheet (FIG. 1) is a side perspective view of a typical tree of 'Autken1' in the early autumn growing in an outdoor nursery.

Figure 2:
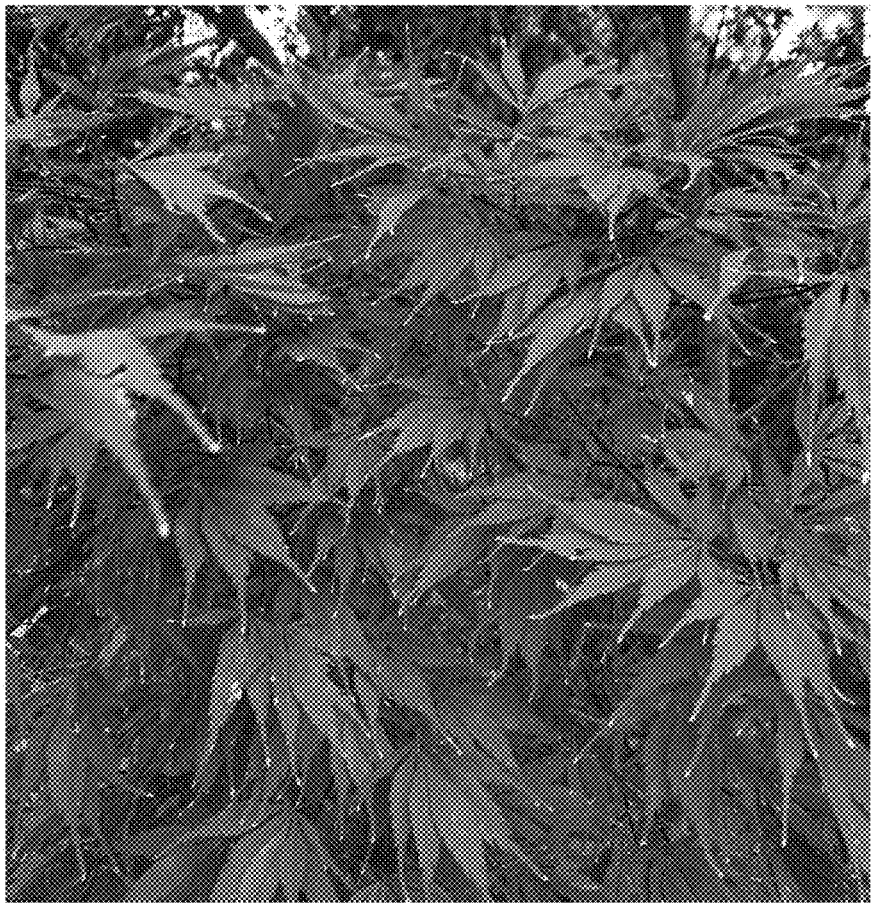

The photograph on the second sheet (FIG. 2) is a close-up view of a typical tree of 'Autken1' in the early autumn growing in an outdoor nursery.

Trees used in the photographs were 15 years old when the photographs were taken and were grown in Cherokee County, Oklahoma.

DETAILED BOTANICAL DESCRIPTION

The following observations, measurements and values describe trees grown in 8-liter containers in an outdoor nursery in Cherokee County, Oklahoma and under cultural practices typical of commercial Japanese Maple tree production. Trees used for the detailed description were two years old and were observed during the summer and autumn. In the following description, color references are made to The Royal Horticultural Society Colour Chart, 2015 Edition, except where general terms of ordinary dictionary significance are used.

Botanical classification: *Acer palmatum* 'Autken1'.

Parentage: Naturally-occurring whole plant mutation of an unnamed selection of *Acer palmatum*, not patented.

Propagation:

*Type*.—By grafting onto a compatible rootstock.

Tree description:

*Plant form and growth habit*.—Deciduous tree with upright to outwardly spreading and inverted triangular form; freely branching habit with lateral branches potentially developing at every node; full and densely-foliated appearance; moderately vigorous growth habit and moderate growth rate.

*Height*.—About 41 cm.

*Width (spread)*.—About 52 cm.

*Trunk caliper, just above graft*.—About 1 cm to 1.2 cm.

*Lateral branch length*.—About 22.5 cm.

*Lateral branch diameter*.—About 5.5 mm.

*Lateral branch internode length*.—About 3.5 cm to 4.25 cm.

*Lateral branch strength*.—Strong, flexible.

*Lateral branch texture and luster*.—When developing: Smooth, glabrous; semi-glossy. Fully developed: Smooth to rough, glabrous; matte; becoming more rough as becoming woody.

*Lateral branch color*.—Initially, close to 187A variably overlain with close to 201A to 201B; becoming closer to 201A to 201B when woody.

Leaf description:

*Arrangement*.—Opposite, simple.

*Length*.—About 7 cm to 7.5 cm.

*Width*.—About 6.8 to 7.75 cm.

*Shape*.—Palmately seven-lobed; sinuses deep and divergent; lobes relatively narrow.

*Apex*.—Sharply acuminate.

*Base*.—Narrowly attenuate.

*Margins*.—Fine and shallow serrations.

*Venation pattern*.—Palmate.

*Texture and luster, upper surface*.—Smooth, glabrous; slightly glossy.

*Texture and luster, lower surface*.—Smooth, glabrous; moderately glossy.

*Color*.—When developing, upper surface: Close to NN137A variably overlain with close to 200A to 200B. When developing, lower surface: Close to NN137A to NN137B. Fully developed, upper surface: Close to 200A to 200B; midvein, close to 200B and lateral venation, close to 200A to 200B; in the autumn, color becoming closer to 53B. Fully developed, lower surface: Close to between NN137A and 147A slightly and variably overlain with close to 200A to 200B; venation, close to NN137A; in the autumn, color becoming closer to 200A to 200B.

*Petioles*.—Length: About 1.8 cm to 2.3 cm. Diameter: About 1 mm. Texture and luster, upper and lower surfaces: Smooth, glabrous; glossy. Strength: Moderately strong, wiry; flexible. Color, upper surface: Close to 144A overlain with close to 200B. Color, lower surface: Close to 144A variably overlain with close to 200B.

Flower description: To date, flower initiation and development has not been observed on plants of the new Japanese Maple tree.

Temperature tolerance: Trees of the new Japanese Maple have been observed to tolerate high temperatures about 45° C. and low temperatures about −20° C.

Pathogen & pest resistance: To date, trees of the new Japanese Maple have not been observed to be resistant to pathogens and pests common to Japanese Maple trees.

It is claimed:

1. A new and distinct Japanese Maple tree named 'Autken1' as herein illustrated and described.

* * * * *